(12) United States Patent
Grado et al.

(10) Patent No.: US 11,468,144 B2
(45) Date of Patent: Oct. 11, 2022

(54) DIGITAL SIGNAL PROCESSING USING SLIDING WINDOWED INFINITE FOURIER TRANSFORM

(71) Applicant: REGENTS OF THE UNIVERSITY OF MINNESOTA, Minneapolis, MN (US)

(72) Inventors: Logan L. Grado, Minneapolis, MN (US); Matthew D. Johnson, Minneapolis, MN (US); Theoden I. Netoff, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 683 days.

(21) Appl. No.: 16/009,829

(22) Filed: Jun. 15, 2018

(65) Prior Publication Data

US 2018/0365194 A1 Dec. 20, 2018

Related U.S. Application Data

(60) Provisional application No. 62/520,265, filed on Jun. 15, 2017.

(51) Int. Cl.
*G06F 17/14* (2006.01)
*A61B 5/00* (2006.01)
(Continued)

(52) U.S. Cl.
CPC ............ *G06F 17/147* (2013.01); *A61B 5/316* (2021.01); *A61B 5/7257* (2013.01); *A61N 1/36196* (2013.01); *G06F 17/141* (2013.01); *A61B 5/318* (2021.01); *A61B 5/374* (2021.01); *A61B 5/389* (2021.01); *A61B 5/4836* (2013.01); *A61B 5/4851* (2013.01); *A61B 5/686* (2013.01); *A61B 2562/0219* (2013.01); *A61N 1/36038* (2017.08); *A61N 1/36171* (2013.01); *H03H 2017/009* (2013.01)

(58) Field of Classification Search
CPC .. G06F 17/14–148; H03H 17/04–0461; H03H 2017/0466–0494
USPC .......................................... 708/400, 402–405
See application file for complete search history.

(56) References Cited

U.S. PATENT DOCUMENTS

| | | | | |
|---|---|---|---|---|
| 2009/0304190 | A1* | 12/2009 | Seefeldt | G10L 25/69 381/56 |
| 2016/0070673 | A1* | 3/2016 | Wang | G06F 17/141 708/403 |
| 2016/0078001 | A1* | 3/2016 | Wang | G06F 17/141 708/405 |

OTHER PUBLICATIONS

D. Patterson and J. Hennessy, Computer Organization and Design, the Hardware/Software Interface, 3rd edition, Elsevier, 2007, ch 1, p. 15-16 (Year: 2007).*

(Continued)

*Primary Examiner* — Emily E Larocque
(74) *Attorney, Agent, or Firm* — Quarles & Brady LLP

(57) ABSTRACT

Systems and methods for digital signal processing using a sliding windowed infinite Fourier transform ("SWIFT") algorithm are described. A discrete-time Fourier transform ("DTFT") of an input signal is computed over an infinite-length temporal window that is slid from one sample in the input signal to the next. The DTFT with the temporal window at a given sample point is effectively calculated by phase shifting and decaying the DTFT calculated when the temporal window was positioned at the previous sample point and adding the current sample to the result.

13 Claims, 9 Drawing Sheets

(51) Int. Cl.
*A61N 1/36* (2006.01)
*A61B 5/316* (2021.01)
*H03H 17/00* (2006.01)
*A61B 5/318* (2021.01)
*A61B 5/374* (2021.01)
*A61B 5/389* (2021.01)

(56) References Cited

OTHER PUBLICATIONS

A. Oppenheim and R. Schafer, Discrete-Time Signal Processing, Prentice Hall, 1989, p. 581-582, 696-699 (Year: 1989).*
M. Manngard et al., Online frequency estimation with applications to engine and generator sets, Mechanical Systems and Signal Processing, Jan. 20, 2017 (Year: 2017).*
K. Duda, Accurate, Guaranteed Stable, Sliding Discrete Fourier Transform, IEEE Signal Processing Magazine, 2010 (Year: 2010).*
L. Grado et al., The Sliding Windowed Infinite Fourier Transform, IEEE Signal Processing Magazine, Sep. 2017 (Year: 2017).*
Jacobsen, E. et al. "An Update to the Sliding DFT," IEEE Signal Process. Mag., 2004; 21(1):110-111.
Jacobsen, E. et al. "The Sliding DFT," IEEE Signal Process Mag., 2003; 20(2):74-80.

* cited by examiner (d) parallel aSWIFT IIR filter (e) direct aSWIFT IIR filter

DIGITAL SIGNAL PROCESSING USING SLIDING WINDOWED INFINITE FOURIER TRANSFORM

CROSS-REFERENCE TO RELATED APPLICATIONS

This application claims the benefit of U.S. Provisional Patent Application Ser. No. 62/520,265, filed on Jun. 15, 2017, and entitled "DIGITAL SIGNAL PROCESSING USING SLIDING WINDOWED INFINITE FOURIER TRANSFORM," which is herein incorporated by reference in its entirety.

STATEMENT REGARDING FEDERALLY SPONSORED RESEARCH

This invention was made with government support under DGE-1069104 and CBET-1264432 awarded by the National Science Foundation, and under NS094206 and NS098573 awarded by National Institutes of Health. The government has certain rights in the invention.

BACKGROUND

The discrete Fourier transform ("DFT") is the standard tool for spectral analysis in digital signal processing, typically computed using the fast Fourier transform (FFT). However, for real-time applications that require recalculating the DFT at each sample or only over a subset of the N center frequencies of the DFT, the FFT is far from optimal.

One alternative to the DFT is the sliding DFT, which was described by E. Jacobsen and R. Lyons in "The Sliding DFT," *IEEE Signal Process Mag.*, 2003; 20(2):74-80, and by E. Jacobsen and R. Lyons in "An Update to the Sliding DFT," *IEEE Signal Process. Mag.*, 2004; 21(1):110-111. The sliding DFT allows for a more efficient computation of the DFT on a sample-by-sample basis by computing individual DFT bins recursively using a finite, rectangular window.

However, the sliding DFT has marginal stability and requires storing N previous inputs, which can be memory intensive for larger signals. Moreover, the rectangular window used for the sliding DFT causes spectral leakage, and is limited to computing the N center frequencies of the DFT.

SUMMARY OF THE DISCLOSURE

The present disclosure addresses the aforementioned drawbacks by providing a method for extracting signal feature data from input signal data. Input signal data that includes a plurality of samples are provided to a computer system. Signal feature data are generated with the computer system by applying a sliding windowed infinite Fourier transform ("SWIFT") to the input signal data. The SWIFT includes selecting a window function that is an infinite-length function having a time constant with units of number of samples. A discrete-time Fourier transform ("DTFT") matrix is then initialized with the computer system, and the DTFT matrix is recursively updated by phase shifting the DTFT matrix by an angular frequency, decaying an amplitude of the DTFT matrix using the time constant, and selecting a next sample in the input signal data and adding the next sample to the DTFT matrix. The updated DTFT is recursively processed in this manner by phase shifting, amplitude decaying, and adding the next sample in the input signal data to generate the signal feature data. The signal feature data generated by the computer system, which includes at least one of amplitude information of the input signal data, phase information of the input signal data, or frequency information of the input signal data, is then stored in the computer system for later use.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
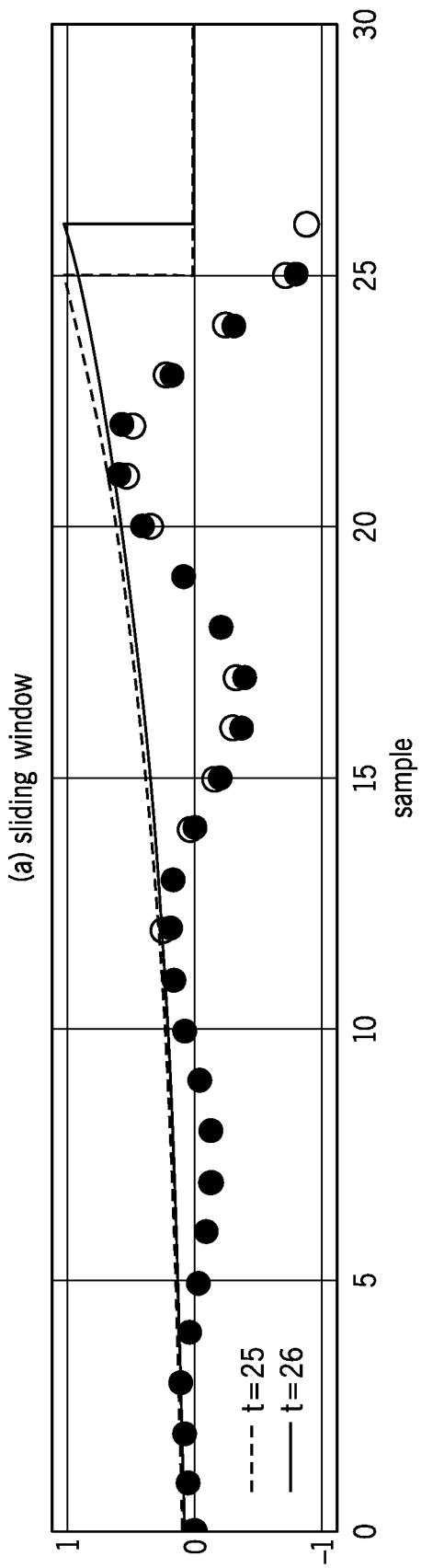
FIG. 1A shows signal windowing function for an example implementation of a sliding windowed infinite Fourier transform ("SWIFT") algorithm. The data samples (circles) and window (solid line) used for the first computation are shown in blue and for the second computation are shown in green.

Described here are systems and methods for digital signal processing using a sliding windowed infinite Fourier transform ("SWIFT") algorithm and a variant called αSWIFT, which may be implemented with a hardware processor and a memory, in order to transform input signal data to signal feature data. Signal feature data may include, for instance, amplitude information, phase information, frequency information, or combinations thereof that are generated from the input signal data. In some instances, the input signal data can be spatial domain data or temporal domain data, and generating the signal feature data can include transforming the spatial domain data or temporal domain data into frequency domain data.

In general, the SWIFT algorithms described in the present disclosure compute a discrete-time Fourier transform ("DTFT") of an input signal over an infinite-length temporal window that is slid from one sample in the input signal to the next. The DTFT with the temporal window at a given sample point is effectively calculated by phase shifting and decaying the DTFT calculated when the temporal window was positioned at the previous sample point and adding the current sample to the result. Compared to existing methods, such as the sliding DFT, the systems and methods described in the present disclosure are stable and allow for improved computational efficiency, improved frequency resolution, improved sampling, reduced memory requirements, and reduced spectral leakage.

Thus, when implemented with a computer system, which may include a hardware processor and a memory, the methods described in the present disclosure improve the functioning of the computer system by reducing the memory requirements otherwise needed to generate signal feature data from input signal data. The methods described in the present disclosure also improve the computational efficiency of the computer system, which as one example can reduce the time and resources (e.g., power consumption, memory requirements, computational cost) needed to generate signal feature data from input signal data.

The systems and methods described in the present disclosure also provide improvements to a range of technical fields. As noted, the systems and methods described in the present disclosure have the advantage of improved frequency resolution, improved sampling, and reduced spectral leakage relative to other methods. These advantages result in improvements to various technical fields, including those described below.

It should be noted that the systems and methods described in the present disclosure can encompass hardware, software, firmware, or any suitable combination thereof.

The SWIFT algorithms described in the present disclosure can be used for a range of different applications where it is desired to produce an accurate, rapid estimation of the phase, amplitude, and instantaneous frequency of a signal, with very little memory or computational requirements. For instance, the SWIFT algorithms can be used in applications for analyzing any suitable digital signal, including physiological signals, auditory signals, accelerometer data, radio waves, and so on.

In general, the SWIFT algorithms can be implemented for real-time, closed-loop systems, especially those that run on small or embedded devices operating at a high sample rate, operating with limited computational resources, operating with limited memory, operating with limited power, or combinations thereof. As an example, the systems and methods described in the present disclosure can therefore enable generating signal feature data from input data on these devices, thus improving their overall functionality. Thus, the SWIFT algorithms are generally applicable in cases where the incoming signal should be processed in real-time; where phase, amplitude, or frequency information should be extracted; and where the resulting information should be acted upon with low latencies.

As one non-limiting example, the SWIFT algorithms described in the present disclosure can be used to process physiological signals, such as signals measured from a subject using a physiological measurement device. In some instances, the physiological signals can be electrophysiological signals and the physiological measurement device can be an electrocardiography ("ECG") device, an electromyography ("EMG") device, and electroencephalography ("EEG") device, or so on. As noted, in some examples the physiological measurement device may be an embedded device, or may be a part of such an embedded device.

As one example, the physiological measurement device may be an ECG device, or another sensor that is operable to measure cardiac electrical activity, that is part of a cardiac implantable electronic device ("CIED"), such as a cardiac resynchronization therapy ("CRT") device, a pacemaker, and so on.

As another example, the SWIFT algorithms can be used in neural stimulation systems, such as those used for providing neural stimulation or Parkinson's disease, essential tremor, dystonia, schizophrenia, Alzheimer's, and other disorders. In the case of neural stimulation, it is becoming increasingly important to be able to measure brain signals and then adapt stimulation parameters accordingly. The phase, amplitude, and instantaneous frequency of the measured neural oscillations can thus be used to adaptively deliver stimulus pulses at the optimal time to disrupt or reinforce an oscillation, or to turn on/off the stimulator when appropriate.

In such examples, the neural stimulation system and include a deep brain stimulation ("DBS") system. The SWIFT algorithms described in the present disclosure can be implemented in a hardware processor and memory that reside in the DBS system, or in a hardware processor and memory that are located external to, but in electrical communication (e.g., wired connection, wireless connection) with, the DBS system. The DBS system may be configured to provide phasic stimulation.

The SWIFT algorithms may be implemented on an EEG device or another sensor that is operable to measure neural oscillations, such as an electrode that is part of the neural stimulator. For instance, a neural stimulator may include a hardware processor and a memory that implement, among other tasks, receiving measured neural oscillations as input data, applying the input data to one or more SWIFT algorithms to generate signal feature data, and storing the signal feature data for subsequent use by the neural stimulator. As noted, the neural stimulator may use the signal feature data to adapt parameters of the electrical stimulation provided by the neural stimulator in response to the measured neural oscillations, which may include adapting those parameters in real-time.

For instance, the SWIFT algorithms can be used to detect how an action (e.g., stimulation) will affect oscillatory activity, and can also be used to predict when to deliver an action. The former can be used to identify when to end stimulation, while the latter can be used to identify when to begin stimulation (e.g., for preventing epileptic seizures, Tourette Syndrome tic manifestation, addiction cravings based on environmental cues). In addition, in these cases and many like it, the stimulator device (e.g., a neural stimulator) is often embedded within the patient, where computational resources, memory, and power are often at a premium.

As another non-limiting example, the SWIFT algorithms described in the present disclosure can be used to process auditory signals, such as those measured with cochlear implants; however, auditory signals measured or generated with other devices can similarly be processed using the SWIFT algorithms described here. Cochlear implants rely on converting incoming auditory signals into electrical stimulation pulses that are applied to the cochlear nerve. Like most neural stimulators, these devices have limited resources. As an example then, the systems and methods described in the present disclosure can improve the functioning of a cochlear implant (e.g., a hardware processor and a memory that are part of such a device) by generating signal feature data from input signal data with increased computation efficiency, reduced memory requirements, or both, which in turn consumes fewer of the limited resources (e.g., power) available to such devices.

The SWIFT algorithms can be used in cochlear implants to extract instantaneous phase, amplitude, and frequency information from an incoming auditory signal, allowing for more precise stimulation. Additionally, for normal perception to occur, it is often desired to have neurons fire in a phase-locked manner in response to an incoming auditory signal. In such instances, the SWIFT algorithms can be used to extract phase information such that a more precise stimulation can be delivered. For example, a cochlear implant may include a hardware processor and a memory that implement, among other tasks, receiving recorded auditory signals as input data, applying the input data to one or more SWIFT algorithms to generate signal feature data, and storing the signal feature data for subsequent use by the cochlear implant. As noted, the cochlear implant may use the signal feature data to adapt parameters of the electrical stimulation provided by the cochlear implant to the cochlear nerve in response to the recorded auditory signals.

As still another non-limiting example, the SWIFT algorithms described in the present disclosure can be used in brain-computer interfaces ("BCIs"), which rely on decoding intent from the strength of neural oscillations recorded using electroencephalography ("EEG") electrodes placed on the scalp. In order to have good control, it is desirable for a BCI system to reliably and quickly extract amplitude information from the subject. The SWIFT algorithms can efficiently extract this information, improving latencies and reducing computational overhead from BCI devices. In this way, the systems and methods described in the present disclosure can improve the functioning of such BCI systems by reducing latencies, which in turn can improve the BCI system's ability to generate control signals in real-time in response to neural oscillations in a subject's brain.

As still another non-limiting example, the SWIFT algorithms described in the present disclosure can be used in speech-to-text and other speech recognition applications. Many speech-to-text algorithms make use of Fourier transforms to extract frequency information from the incoming audio signal. The SWIFT algorithms described in the present disclosure can be used to efficiently extract frequency information from the incoming audio signal in such applications. In some instances, speech-to-text and speech recognition applications may be implemented with a hardware processor and a memory that are part of a mobile device, such as a smart phone, that has limited resources (e.g., limited power available from a battery). As such, the systems and methods described in the present disclosure can improve the functioning the mobile device by reducing the power consumption needed for implementing speech-to-text and speech recognition applications through the improved computational efficiency and reduced memory requirements enabled by the SWIFT algorithms.

As still another non-limiting example, the SWIFT algorithms described in the present disclosure can be used to process signals generated by wearable devices, which may include signals generated by inertial sensors such as accelerometer, gyroscopes, magnetometers, and so on. For instance, the wearable device can include a wrist-mounted inertial sensor (e.g., accelerometer, gyroscope, combinations thereof) and the signals generated by the inertial sensor can be provided as input signal data to the SWIFT algorithms described in the present disclosure. The phase data, amplitude data, or both, that are generated can be used to measure tremor. In some instances, the wearable device may include a hardware processor and a memory, and in other instances the wearable device may be in electrical communication (e.g., wired connection, wireless connection) with a mobile device, such as a smart phone, that has a hardware processor and memory implementing the SWIFT algorithms described in the present disclosure. In either case, the wearable device and the mobile device both have limited resources (e.g., limited power available from a battery). As such, the systems and methods described in the present disclosure can improve the functioning the wearable device, the mobile device, or both, by reducing the power consumption needed for generating signal feature data from signals recorded or otherwise measured with the wearable device through the improved computational efficiency and reduced memory requirements enabled by the SWIFT algorithms.

It will be appreciated by those skilled in the art that the SWIFT algorithms described in the present disclosure can be used in applications other than those explicitly provided above. For instance, the SWIFT algorithms described in the present disclosure can be used in other applications, including industrial controls, data compression, and other fields. Moreover, the SWIFT algorithms described in the present disclosure can be implemented for digital image processing applications, which may be implemented for processing medical images or other types of digital images. As with the examples provided above, in these other instances it will be appreciated that the systems and methods described in the present disclosure can improve the functioning of the computer system implementing the SWIFT algorithms by increasing computation efficiency and reducing memory requirements. As noted above, the systems and methods described in the present disclosure can also improve the technical applications for which they are implemented, such as by improving frequency resolution, improving sampling, and reducing spectral leakage.

Before describing the SWIFT algorithms, the sliding DFT ("SDFT") is revisited. The SDFT performs an N-point DFT on samples within a sliding rectangular window. The DFT is initially computed on the first N samples. The time window is then advanced one sample and a new N-point DFT is calculated directly from the results of the previous DFT. The SDFT can thus be expressed compactly as, $$X_n[k] = X_{n-1}[k] e^{j2\pi k/N} - x[n-N] + x[n] \tag{1}$$

The SDFT's output is discrete in frequency space, and is limited to normalized frequencies of $2\pi k/N$ for $k \in \mathbb{Z}$.

The single-bin SDFT algorithm can be implemented as an infinite-impulse response ("IIR") filter with a comb filter followed by a complex resonator. Such IIR filters can be implemented as software, or as hardware using appropriate electronic circuitry. The recursive nature of the SDFT dictates that some initialization method is required. That is, the output, $X_n[k]$, is only valid if $X_{n-1}[k]$ was valid.

There are two methods for initializing the SDFT algorithm. In the first initialization approach, all $X_{n-1}[k]$ values are reset to zero, after which cycling of the data begins. After N samples have cycled, the output will be valid. In the second approach to initializing the SDFT algorithm, all $X_{n-1}[k]$ values are initialized with an FFT of the previous N samples.

While the SDFT is an efficient algorithm, use of a rectangular window results in spectral leakage. To address this, time-domain windowing via frequency-domain convolution can be implemented, which can be done with almost any finite window, but this solution significantly increases the computational complexity and compromises the simplicity of the SDFT.

The SWIFT algorithms described in the present disclosure address the drawbacks of the SDFT algorithm. For instance, the SWIFT algorithms can reduce spectral leakage without increasing computational complexity and improve frequency-domain sampling. The SWIFT algorithms can also give more weight to more recent samples, which allows for improved real-time spectral and phase analysis.

As mentioned above, the SWIFT algorithm can be viewed as a type of sliding DTFT windowed with an infinite-length temporal window function. As one example, the temporal window function is an infinite-length, causal, exponential function, $$w[m] = \begin{cases} e^{m/\tau} & m \leq 0 \\ 0 & m > 0 \end{cases}; \quad (2)$$

where $w[m]$ is the window function, $m=0$ is the current sample, and $\tau>0$ is the time constant of the window in units of samples. The exponential window gives more weight to more recent samples, allowing the SWIFT algorithm to be more sensitive to transient changes in signal power than a rectangular window. It will be appreciated, however, that other infinite-length window functions could be implemented with similar effect. The exponential windowed DTFT is, $$X_n(\omega) = \sum_{m=-\infty}^{0} e^{m/\tau} x[n+m] e^{-j\omega m}; \quad (3)$$

where $\omega$ is an angular frequency that is continuous in frequency space and has normalized units of radians per sample (i.e., $\omega=2\pi f/f_s$). A recursive formula for Eqn. (3) can be described by relating $X_{n+1}(\omega)$ back to $X_n(\omega)$ as follows, $$X_{n+1}(\omega) = e^{-1/\tau} e^{j\omega} X_n(\omega) + x[n+1] \quad (4).$$

The result of Eqn. (4) can be decremented by one sample to yield the following recursive SWIFT formulation:

$$X_n(\omega) = e^{-1/\tau} e^{j\omega} X_{n-1}(\omega) + x[n] \quad (5).$$

The SWIFT algorithm operates, in general, by rotating the phase of the previous DTFT by $\omega$ (i.e., phase shifting the previous DTFT), decaying the amplitude of the previous DTFT by $e^{-1/\tau}$, and adding in the new data sample, $x[n]$. The SWIFT algorithm can therefore be implemented with one complex multiplication and one real addition per sample per frequency bin. As an example, implementations of SWIFT can include recursively computing the windowed DTFT using Eqn. (5), whereby the previous DTFT is phase shifted by the angular frequency and amplitude decayed according to the time constant of the window. In some embodiments, the recursion can be initialized by computing $X_0$ as a DTFT on previous samples. In some other embodiments, the recursion can be initialized by computing $X_0$ based on another transformation, such as an FFT of previous samples, similar to the methods for initializing an SDFT described above. In still other embodiments, the recursion can be initialized by setting $X_0$ as a selected value, which may be $X_0=0$.

FIG. 1A shows an example of how the SWIFT's window advances one sample at a time, picking up the new data sample and updating the previous samples. The incremental advance and infinite nature of the time window leads to the name sliding windowed infinite Fourier transform.

Like the SDFT, the SWIFT algorithms described in the present disclosure can be initialized by sliding onto the data, or by calculating the DTFT with a window (e.g., the exponential window described above) on all previous data.

The z-domain transfer function of the SWIFT filter with normalized angular frequency, $\omega$, can be given by, $$H_{SWIFT}(z) = \frac{1}{1 - e^{-1/\tau} e^{j\omega} z^{-1}}. \quad (6)$$

Figure 1B:
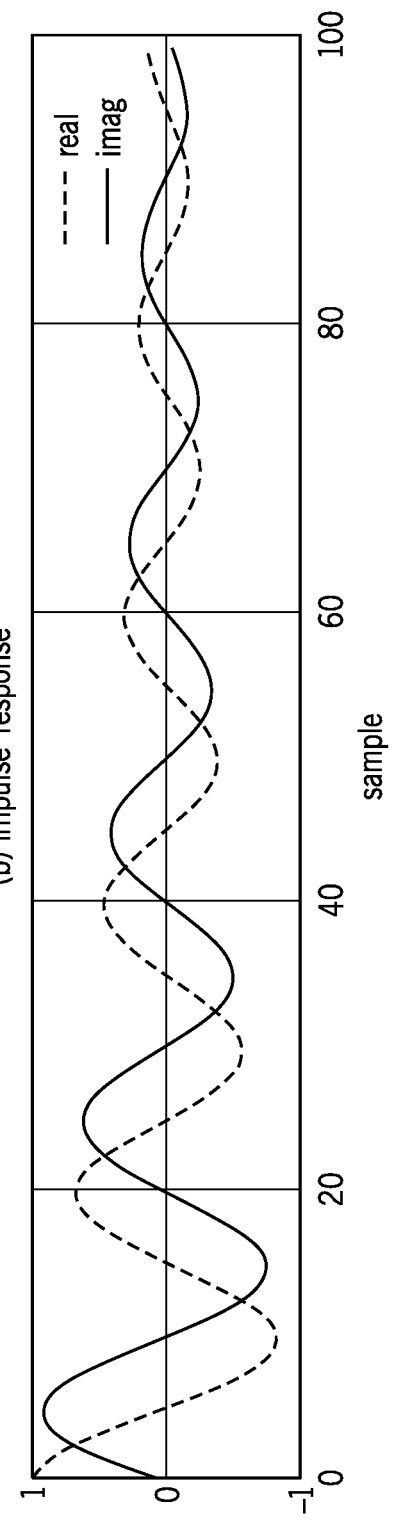
FIG. 1B is the impulse response of the SWIFT examples shown in FIG. 1A.
Figure 1C:
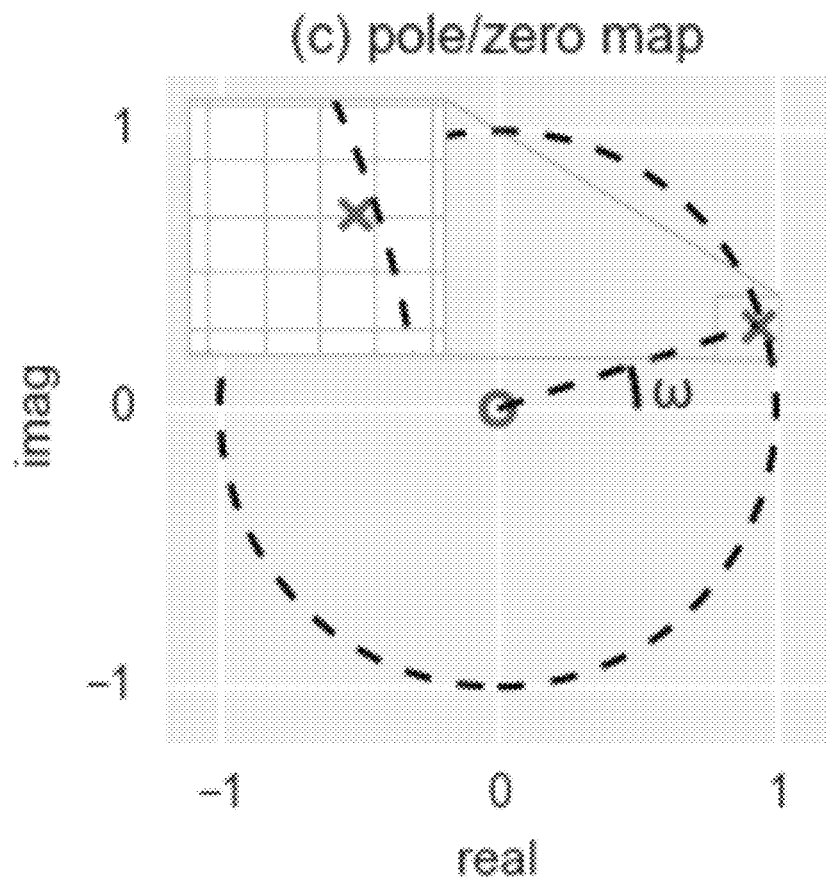
FIG. 1C is a pole-zero plot for a single bin SWIFT with $\tau=50$ samples and $\omega=\pi/10$ radians per sample.

The SWIFT IIR filter has one zero at the origin and a single pole lying inside the unit circle at $e^{-1/\tau} e^{j\omega}$. An example of the impulse response of the SWIFT algorithms is shown in FIG. 1B, and a pole-zero plot is shown in FIG. 1C, with $\tau=50$ samples and $\omega=\pi/10$ radians per sample.

Figure 1D:
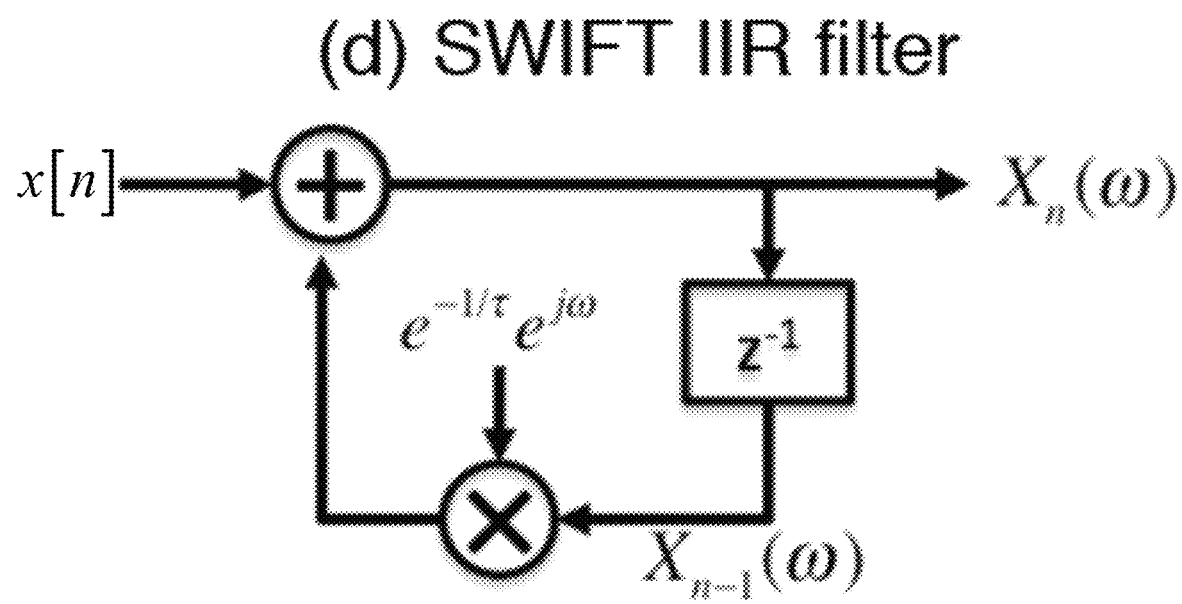
FIG. 1D is an example of an infinite impulse response ("IIR") filter representation of a SWIFT algorithm.

Like the SDFT algorithm, the SWIFT algorithm can be implemented as an IIR filter with a complex resonator, as shown in FIG. 1D. Unlike SDFT, the SWIFT filter does not require a comb filter. Thus, with the SWIFT algorithm, an arbitrary number of frequency bins can be calculated by adding more complex resonators at the desired frequencies.

The SWIFT algorithm has several advantages over SDFT, which are summarized below.

The SWIFT algorithm is more efficient than SDFT. Both SWIFT and SDFT share the property that the number of computations required to calculate $X_n(\omega)$ (or $X_n[k]$) from $X_{n-1}(\omega)$ (or $X_{n-1}[k]$) is fixed and independent of the window length. However, the SWIFT algorithm can be implemented with one complex multiplication and one real addition to compute the next output, whereas SDFT requires one complex multiplication and two real additions.

In addition to increased computational efficiency, the SWIFT algorithm has drastically reduced memory requirements compared to those of SDFT. Both the SWIFT and SDFT algorithms store one previous complex output and one complex constant (four floating points). However, the SDFT algorithm must also store N previous input samples, while the SWIFT algorithm does not require storing previous input samples. The storage and retrieval of N previous samples, as required by SDFT algorithms, can be a significant limitation for implementing SDFT algorithms in small sensors and embedded devices. The SWIFT algorithms described in the present disclosure address and overcome these drawbacks of the SDFT algorithm, thereby providing a significant improvement to the functioning of the computer system, embedded device, or hardware processor.

The SDFT algorithm's output, as a type of DFT, is limited to normalized frequencies of $2\pi k/N$, where k is an integer. In order to achieve finer frequency-domain sampling, SDFT requires a larger number of samples, N, which reduces the temporal resolution and produces a tradeoff between time and frequency resolution. On the other hand, the SWIFT algorithm's output, as a type of DTFT, is continuous in the frequency domain, which provides greater flexibility in tuning the frequencies of interest.

When operating multiple SWIFT algorithms in parallel, each time constant, τ, can be tuned to a different frequency bin of interest without increasing computational complexity. For instance, the time constant, τ, can be set as a multiple of the period, such that τ=c/f, where c is a unitless constant and f is the center frequency. Conversely, to achieve a similar effect with parallel SDFT algorithms, additional comb filters need to be added for each SDFT bin, which further increases the computational complexity and memory requirements of implementing the SDFT. The SWIFT algorithm can therefore be implemented with a multi-resolution property, which can be used to provide better time resolution at higher frequencies and better frequency resolution at lower frequencies.

The SWIFT is guaranteed stable, whereas the SDFT is only marginally stable. The SWIFT is guaranteed stable because its pole resides within the unit circle in the Z-domain. In contrast, the SDFT algorithm's pole resides on the unit circle in the Z-domain, which can cause instabilities if numerical rounding causes the pole to move outside the unit circle.

As mentioned above, the SWIFT algorithm has reduced spectral leakage compared to the SDFT. The reduced spectral leakage results from the SWIFT algorithm using an exponential window, or other window with similar effect, as compared to the rectangular window used in the SDFT. The spectral leakage of the SWIFT algorithm can be reduced even further by implementing a second temporal window. In these implementations, the SWIFT algorithm can be referred to as an αSWIFT algorithm.

In general, the spectral leakage of the SWIFT algorithm can be further mitigated by removing the temporal window's discontinuity at m=0. The discontinuity can be removed by modifying the window function to be the difference of two functions (e.g., the difference of two exponentials), $$w_\alpha[m] = \begin{cases} e^{m/\tau_{slow}} - e^{m/\tau_{fast}} & m \leq 0 \\ 0 & m > 0 \end{cases}; \quad (7)$$

where $\tau_{slow} > \tau_{fast} > 0$. The window function, $\omega_\alpha[m]$, can be referred to as the alpha functions (or α function), which goes smoothly to zero at m=0.

Figure 2:
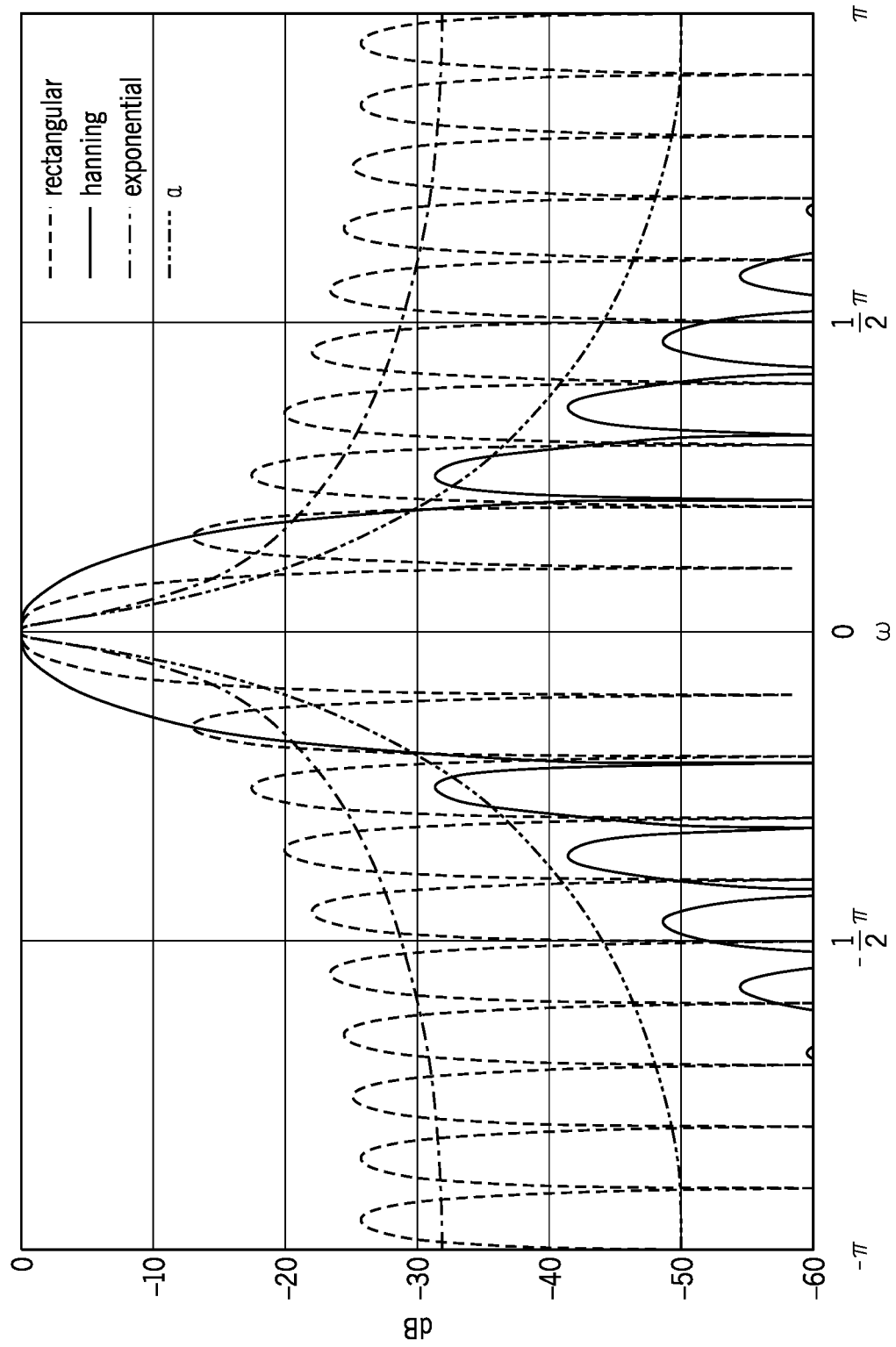
FIG. 2 shows normalized Fourier transforms of four windows: rectangular (blue, N=20), Hanning (black, N=20), SWIFT (green, $\tau=20$) and $\alpha$SWIFT (red $\tau_{slow}=20$, $\tau_{fast}=4$).

FIG. 2 compares the spectral leakage of the alpha window function against a single exponential window function, a rectangular window function, and a Hanning window function. The αSWIFT algorithm was compared to the Hanning SDFT, which is among the simplest windowed SDFTs. As compared to the exponential window, the alpha window has a similarly narrow main lobe, but has significantly faster fall off at the surrounding frequencies. On the other hand, the Hanning window has a significantly wider main lobe, but its side lobes fall off faster than the alpha window function.

Figure 3A:
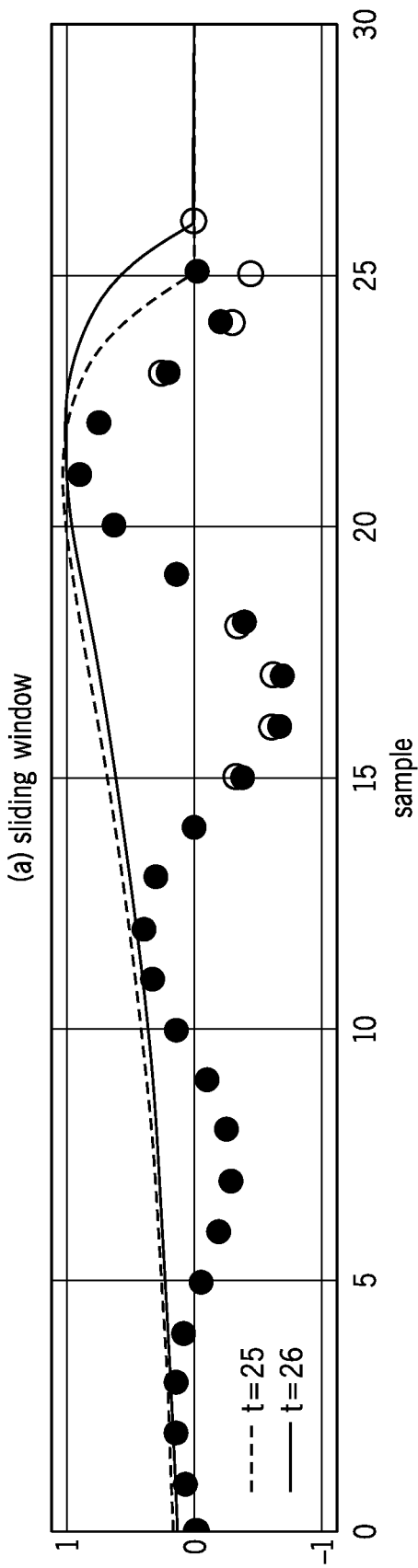
FIG. 3A shows signal windowing for an example implementation of an $\alpha$SWIFT algorithm. The data samples and window used for the first computation are shown in blue and for the second computation are shown in green.

The αSWIFT algorithm can be presented as the difference between two SWIFTs with different time constants through the linearity property of the Fourier transform, $$X_n(\omega)_\alpha X_n(\omega)_{slow} - X_n(\omega)_{fast} \quad (8);$$

where $X_n(\omega)_\alpha$ is the αSWIFT, and $X_n(\omega)_{slow}$ and $X_n(\omega)_{fast}$ are individual SWIFTs with time constants, τ, equal to the slow and fast time constants, respectively. The form of the αSWIFT shown in Eqn. (8) can be referred to as the parallel form of the αSWIFT, which can be seen operating on an example input signal in FIG. 3A.

The Z-domain transfer function of Eqn. (8) can be determined by substituting in Eqn. (6), one for each of the slow and fast SWIFTs, to yield the following:

$$H_{\alpha SWIFT} = \frac{(\beta - \gamma)z^{-1}}{1 - (\beta + \gamma)z^{-1} + \beta\gamma z^{-2}}; \quad (9)$$

where $$\beta = e^{-1/\tau_{slow}} e^{j\omega} \quad (10);$$

$$\gamma = e^{-1/\tau_{fast}} e^{j\omega} \quad (11);$$

Figure 3B:
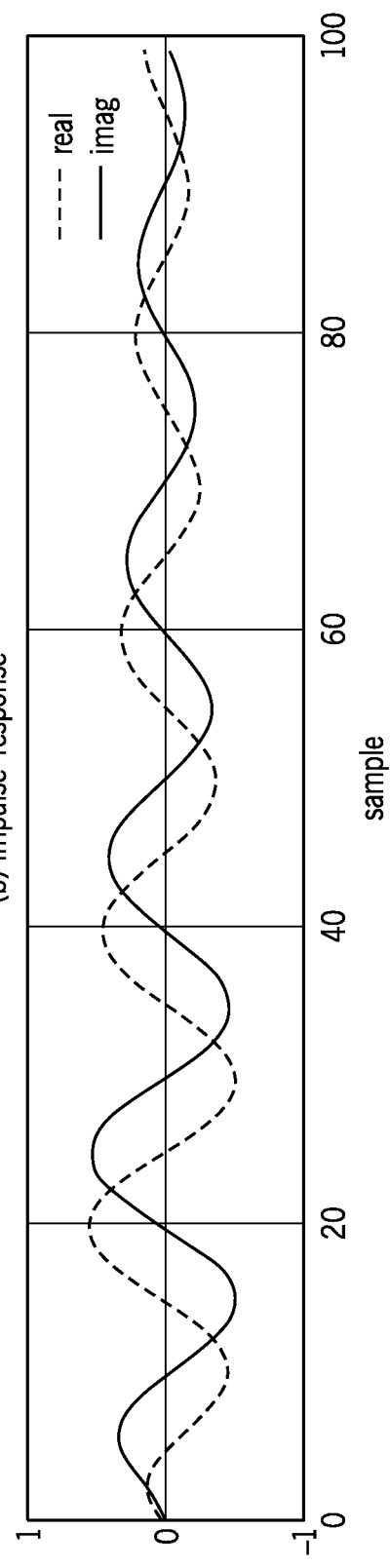
FIG. 3B is the impulse response of the $\alpha$SWIFT examples shown in FIG. 3A.
Figure 3C:
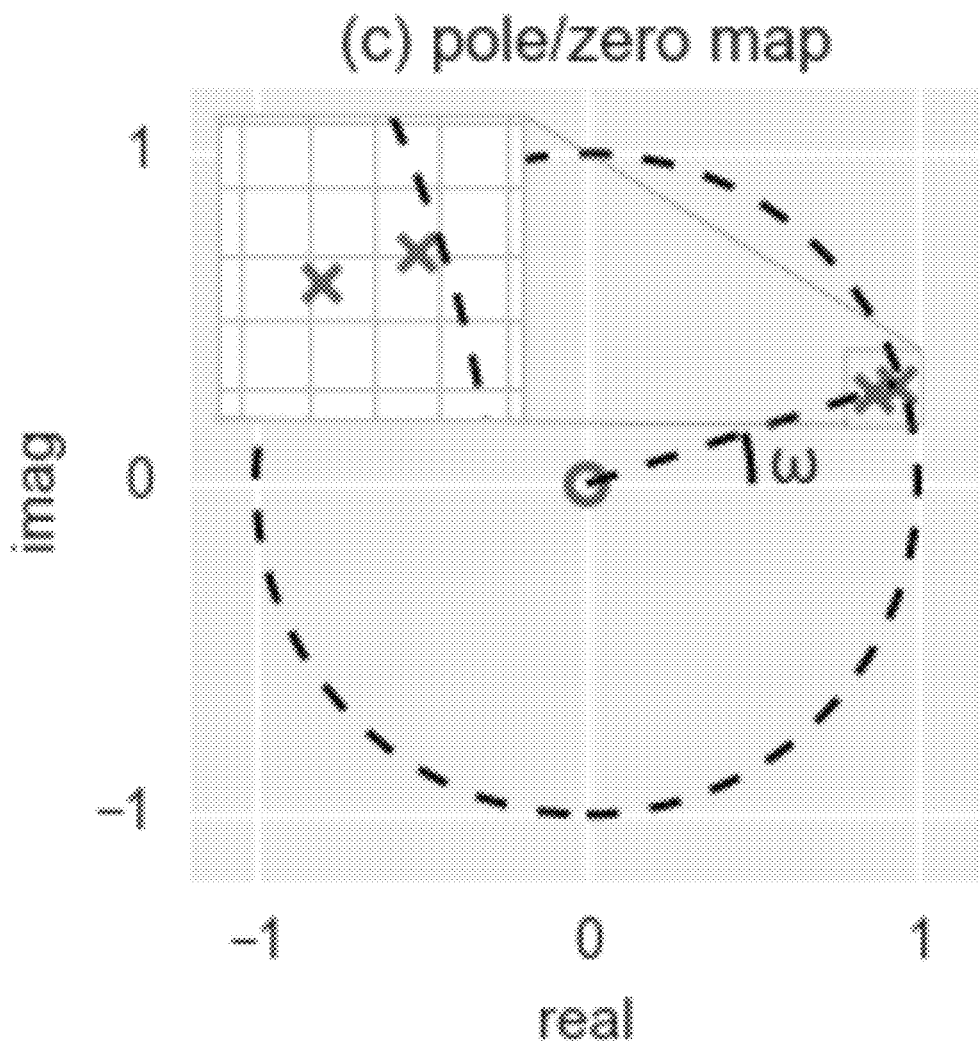
FIG. 3C is a pole-zero plot for a single bin $\alpha$SWIFT with $\tau_{slow}=50$ samples, $\tau_{fast}=10$ samples, and $\omega=\pi/10$ radians per sample

From this form, the poles and zeros of the system can be readily analyzed. The discrete difference form of the αSWIFT can then be derived from the inverse Z-transform of Eqn. (9), $$X_n(\omega)_\alpha = (\beta+\gamma)X_{n-1}(\omega)_\alpha - \beta\gamma X_{n-2}(\omega)_\alpha + (\beta-\gamma)x[n-1] \quad (12);$$

which can be referred to as the "direct form." The impulse response of the αSWIFT is shown in FIG. 3B, and its pole-zero plot is shown in FIG. 3C, with $\tau_{slow}$=50 samples, $\tau_{fast}$=10 samples, and ω=π/10 radians per sample.

Figure 3D:
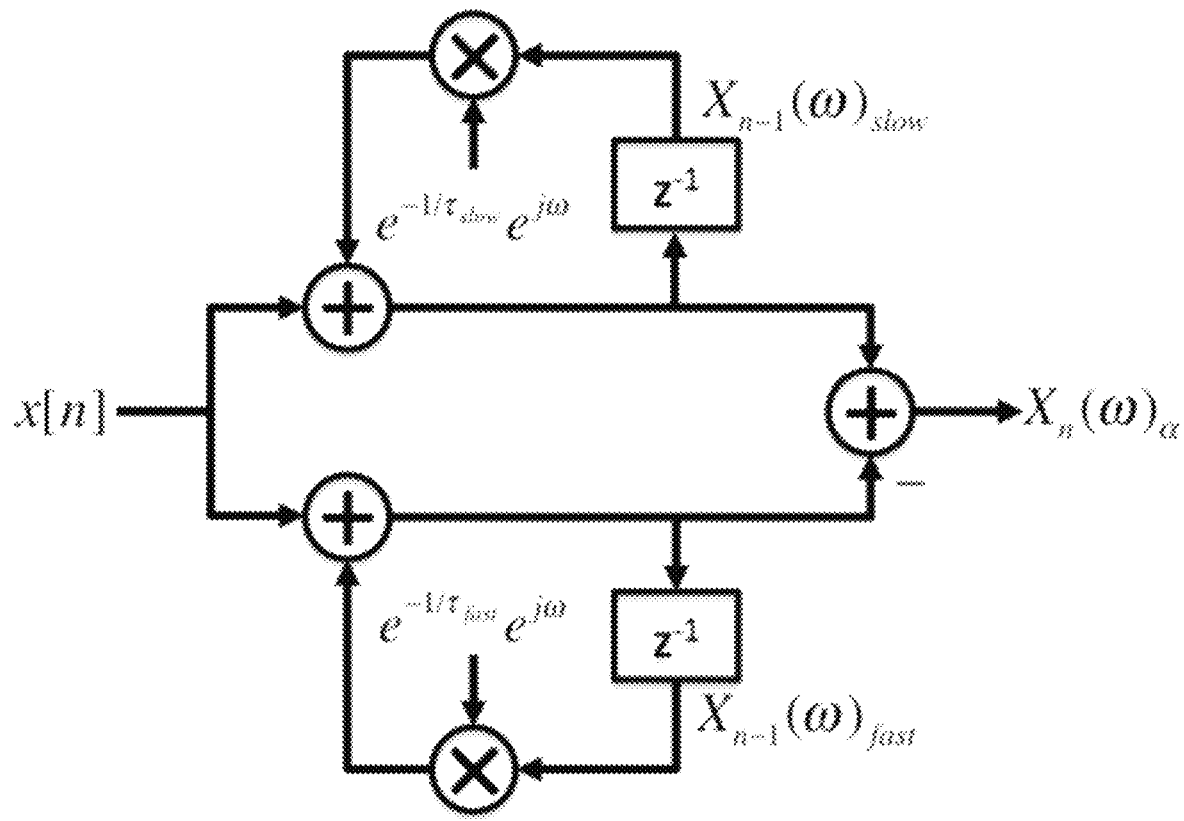
FIG. 3D is an example of an IIR filter representation of a parallel form $\alpha$SWIFT algorithm.
Figure 3E:
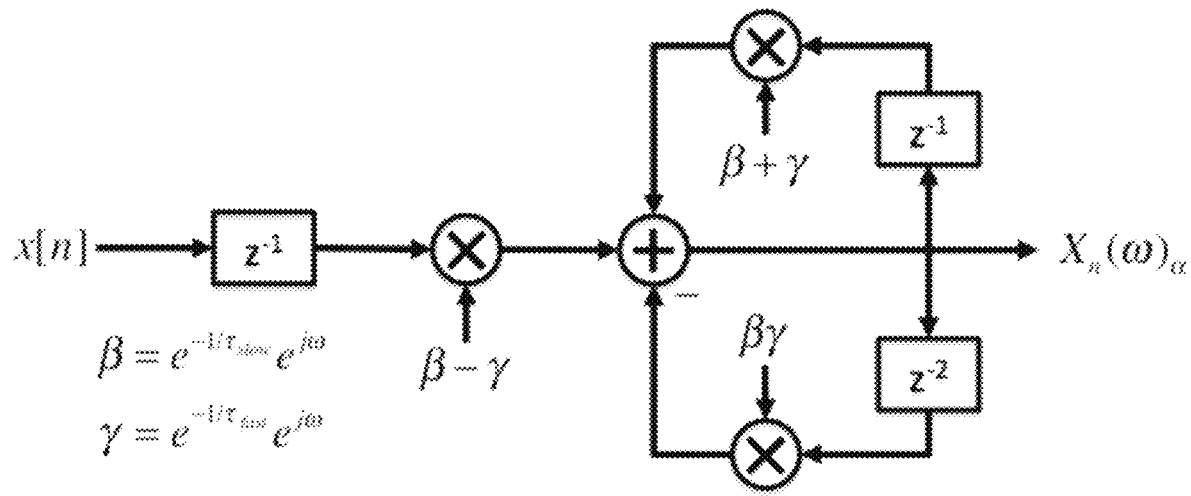
FIG. 3E is an example of an IIR filter representation of a direct form $\alpha$SWIFT algorithm.

Like the SWIFT algorithm, the αSWIFT algorithm can also be implemented as an IIR filter, in either the parallel or direct form. An example of the parallel form IIR filter is shown in FIG. 3D and an example of the direct form IIR filter is shown in FIG. 3E. Both filters produce identical impulse responses and pole-zero plots. The parallel form can be implemented more efficiently than the direct form by using three fewer memory locations (8 floating points versus 11), and two fewer real multiplications to compute the next $X_n(\omega)_\alpha$. Such IIR filters can be implemented as software, or as hardware using appropriate electronic circuitry.

Figure 4:
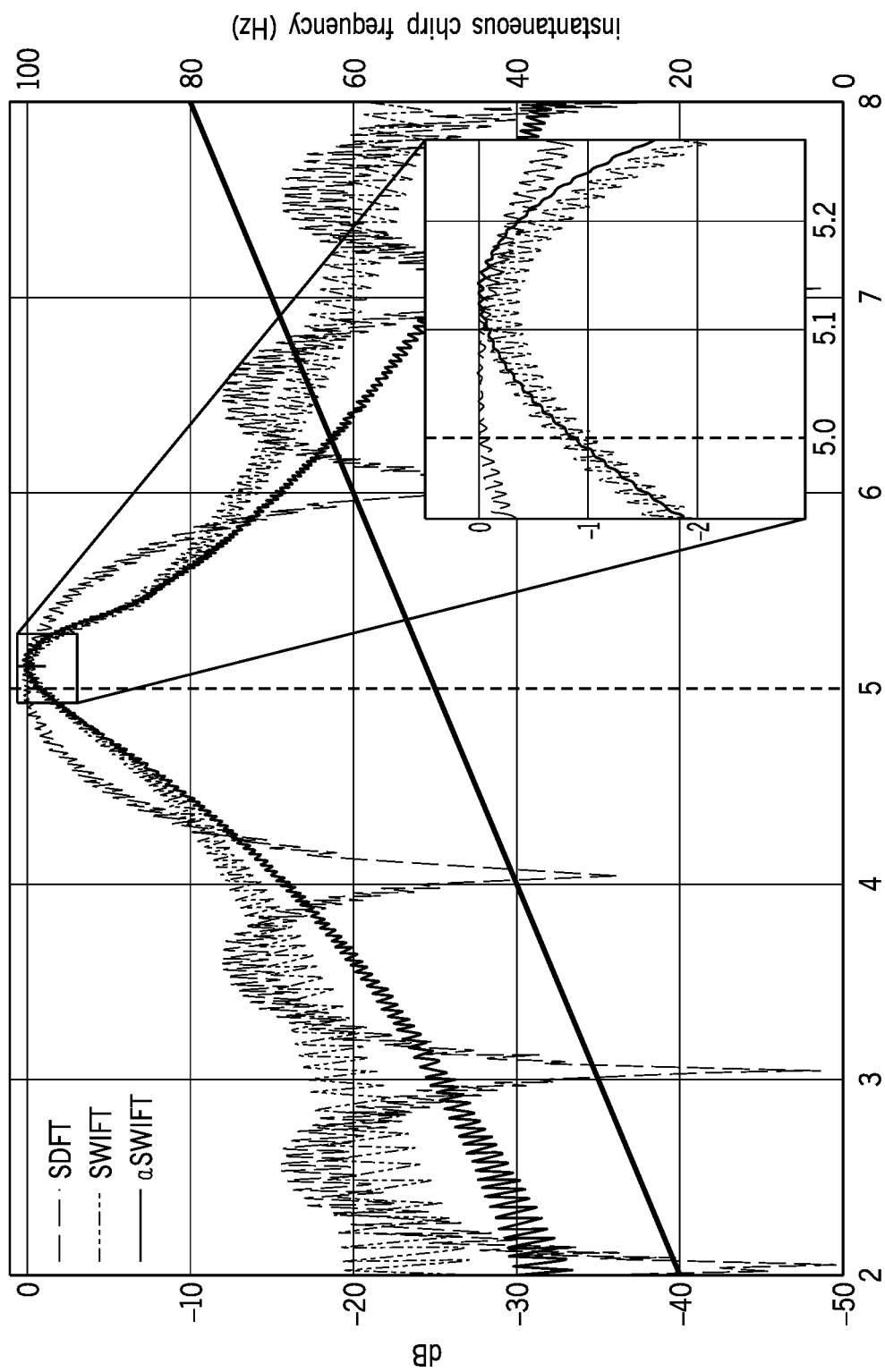
FIG. 4 depicts a comparison of a sliding discrete Fourier transform (N=100), SWIFT ($\tau=72.1$), and $\alpha$SWIFT ($\tau_{slow}=72.1$, $\tau_{fast}=14.2$) with center frequencies at 50 Hz and comparable window lengths operating on a chirp signal (sampling frequency, $f_s=1$ kHz). The frequency axis for the chirp signal is shown on the right-hand side of the figure.

FIG. 4 depicts a comparison between an SDFT, SWIFT, and αSWIFT operating on an example chirp signal. In this example, each transform's center frequency was set at 50 Hz, which the chirp crosses at 5 seconds into the simulation (denoted by the dashed black line). To facilitate comparison, each window was set to have the same half-mass (the number of samples in which half of the area of the window is contained); the SDFT's rectangular window, with N=100, has a half-mass of 50 samples. In this example, the SWIFT's exponential window was set with τ=72.1, providing a half-mass of 50 samples. As compared to the SDFT, both the SWIFT and αSWIFT have narrower peaks and less spectral leakage. In addition, both the SWIFT and SDFT have noise in their outputs, which is reduced in the αSWIFT.

Figure 5:
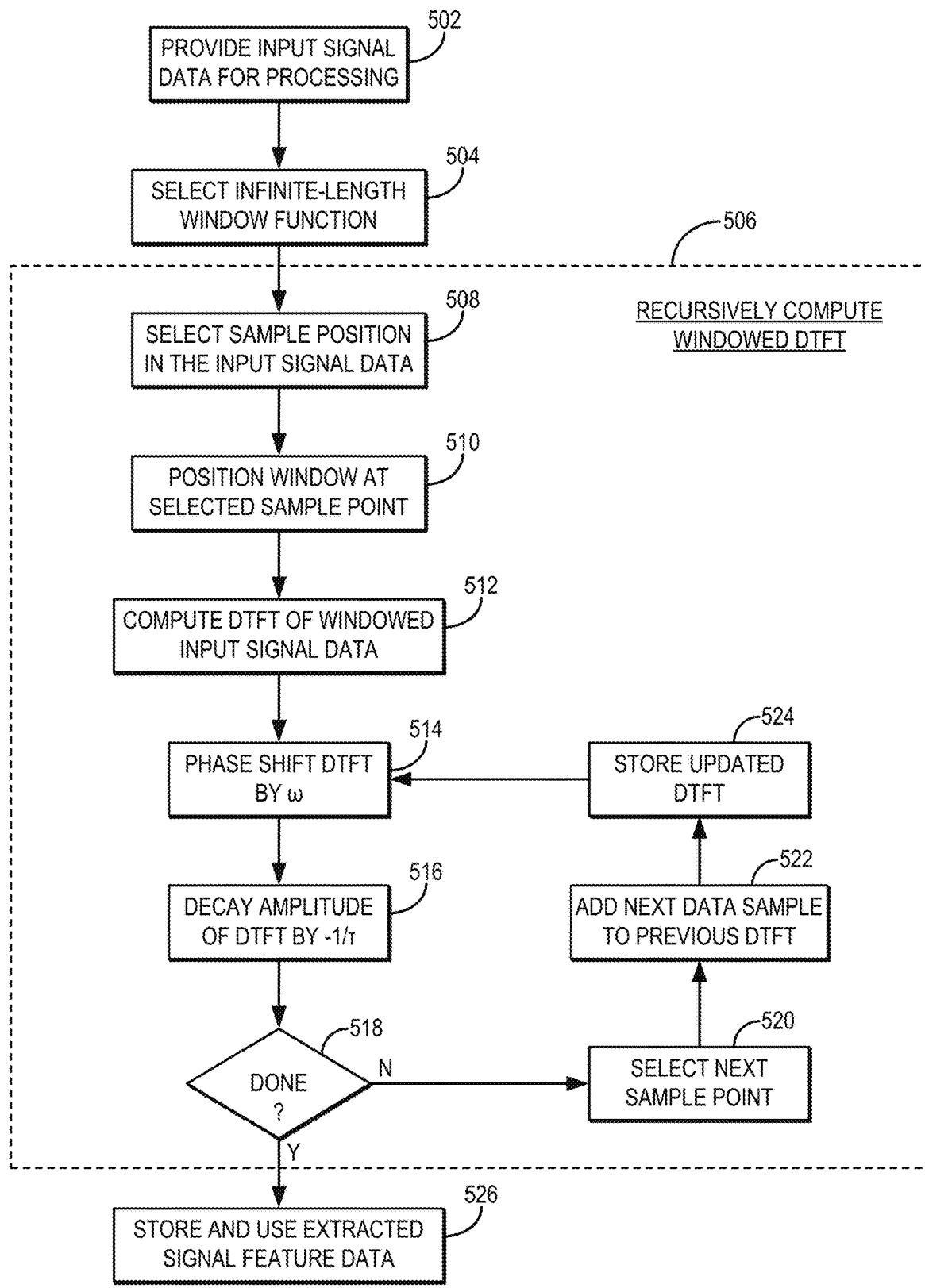
FIG. 5 is a flowchart setting forth the steps of an example method for generating signal feature data from input signal data using a sliding windowed infinite Fourier transform ("SWIFT") according to some embodiments described in the present disclosure.

Referring now to FIG. 5, a flowchart is illustrated as setting forth the steps of an example method for processing an input signal using a SWIFT algorithm to transform that input signal into, or to otherwise generate, signal feature data, such as amplitude, phase, and frequency information extracted from the input signal.

The method includes providing input signal data to a computer system for processing, as indicated at step 502. In some instances, providing the input signal data can include accessing or otherwise retrieving previously measured or acquired input signal data from a memory or other data storage. In some other instances, providing the input signal data can include measuring or otherwise acquiring input signal data with a measurement system or device and providing those input signal data to the computer system, which may be a part of the measurement system or device. As noted above, the computer system can generally include a hardware processor and a memory. In some instances, the computer system can include such a hardware processor and memory implemented in an embedded device. The input signal data can include one or more input signals, which may be any suitable digital signal to be processed.

As one non-limiting example, the input signal data can include one or more physiological signals acquired with a physiological measurement device. For instance, the input signal data can include electrophysiological signals acquired with an electrophysiological measurement device, such as an ECG device, and EEG device, and EMG device, or the like. In some example, the input signal data can be signals representative of neural activity or neural oscillations and thus may be referred to as neural signals, which can be acquired or otherwise measured with an EEG device, a magnetoencephalography ("MEG") device, or the like.

As another non-limiting example, the input signal data can include one or more auditory signals. In some instances, the input signal data can include auditory signals recorded or otherwise acquired with a cochlear implant. In some other instances, the input signal data can include auditory signals recorded or otherwise acquired with a microphone or other auditory recording device, which may be a part of a device such as a phone, a computer, or the like.

Referring still to FIG. 5, the method includes selecting an infinite-length window function, as indicated at step 504. Selecting the infinite-length window function can include selecting one or more time constants, $\tau$, which may be selected based at least in part on characteristics of the input signal data. For instance, as described above, the time constant, $\tau$, can be selected based at least in part on a frequency bin of interest. As one example, the time constant can be selected as $\tau=c/f$, where c is a constant and f is the center frequency of a frequency bin of interest.

As described above, the infinite-length window function is preferably an infinite-length exponential window function; however, it is contemplated that the algorithms described in the present disclosure can be adapted and derived for other infinite-length window functions. In some implementations, the infinite-length window function includes the difference between two infinite-length exponential functions, as described above with respect to the $\alpha$SWIFT algorithm. In such instances, a different time constant can be selected for each window function to generate the infinite-length window function.

As indicated generally at process block 506, a windowed DTFT, $X_n(\omega)$, is recursively computed in order to extract signal feature data from the input signal data. As described above, the recursion can be initialized by setting $X_0$ equal to a DTFT computed on previous data (e.g., input signal data windowed with the window function), an FFT, a selected value (e.g., $X_0=0$), and so on. A first sample position in the input signal data is selected, as indicated at step 508. The window is positioned at this first sample point, as indicated at step 510, and the discrete-time Fourier transform ("DTFT") of the input signal data over the window is computed, as indicated at step 512. As noted, in an initial step the initial value for the DTFT, $X_0$, can be computed on previous data using a DTFT or other transform, or may be a selected value such as $X_0=0$. In subsequent steps, computing the DTFT may include, for example, generating a DTFT matrix by computing the DTFT of the samples in the input signal data as windowed by the window. For instance, the exponential windowed DTFT shown in Eqn. (3) can be computed. For the $\alpha$SWIFT implementations, a windowed DTFT is computed for each window (e.g., the slow window and the fast window). The resulting DTFT is then phase shifted by the angular frequency, $\omega$, as indicated at step 514, and the amplitude of the DTFT is decayed using the time constant, $\tau$, of the window function, as indicated at step 516. Thus, in these steps, a phase shifted DTFT matrix and an amplitude decayed DTFT matrix can be generated, respectively. For instance, the phase shifting and amplitude decaying can be implemented according to Eqn. (5) for the SWIFT implementation or according to Eqns. (8) or (12) for the $\alpha$SWIFT implementation.

A determination is then made at decision block 518 whether the desired amount of input signal data has been processed. If not, then the next sample point in the input signal data is selected, as indicated at step 520, and the next data sample is added to the previous DTFT, which has been phase shifted and amplitude decayed, as indicated at step 522. The result of this step is stored as the DTFT from the previous iteration, as indicated at step 524. The method then recursively proceeds by phase shifting and amplitude decaying the DTFT from the previous iteration until all of the input signal data have been processed, or until some other stopping criterion is satisfied. The resulting final DTFT is then output and stored, as indicated at step 526. As mentioned above, the output can include signal feature data, such as amplitude information of the input signal data, phase information of the input signal data, frequency information of the input signal data, or combinations thereof. In some instances, then, the output may include a visual depiction of the signal feature data generated from the input signal data. Such a visual depiction may be generated on a display. In some implementations, the visual depiction can include generating a graphical display element representative of the signal feature data and displaying the graphical display element on the display.

The signal feature data can be used to control the operation of an electrical stimulation device. In those instances where the input signal data indicated neural signals, the electrical stimulation device can be a neural stimulation device, such as a deep brain stimulation ("DBS") device, or the like. In those instances where the input signal data indicated cardiac electrical activity, the electrical stimulation device can be a cardiac resynchronization therapy ("CRT") device or other cardiac implantable electronic device ("CIED"). In some implementations, the signal feature data are transformed into control signals for operating the electrical stimulation device. For instance, the signal feature data can be transformed into control signals that indicate the relevant operating parameters for delivering the appropriate electrical stimulation by the electrical stimulation device.

The signal feature data can also be used to control the operation of a cochlear implant. For instance, the input signal data can include auditory signals, and the signal feature data extracted from those auditory signals can be used to generate electrical stimulation pulses that are applied to the cochlear nerve by the cochlear implant. Controlling the operation of the cochlear implant can also include using the signal feature data to provide electrical stimulation to the cochlear nerve that results in phase-locked neuronal firing. In some implementations, the signal feature data are transformed into control signals for operating the cochlear implant. For instance, the signal feature data can be transformed into control signals that indicate the relevant operating parameters for delivering the appropriate electrical stimulation by the electrical stimulation device.

The signal feature data can also be used to control the operation of a brain-computer interface ("BCI"). For instance, the input signal data can include neural signal data measured or otherwise acquired with an EEG device. The amplitude information extracted from these input signal data can then be used to provide control of the BCI. As an example, the strength of neural oscillations represented by the extracted amplitude data can be decoded to infer intent of the subject. In some implementations, the signal feature data are transformed into control signals for operating the BCI system. For instance, the signal feature data can be transformed into control signals that indicate the relevant operating parameters for controlling a device that is in communication with the BCI system, such as a prosthetic device.

The signal feature data can also be used in speech recognition and other auditory signal processing applications. In such instances, the input signal data includes auditory signals, such as those recorded or otherwise acquired with a microphone, which may be a separate device or part of a cellular device, a computer, or the like. The frequency information and other signal feature data extracted from these input signal data can then be processed for speech-to-text applications, to improve the quality of the auditory signal, or to provide other processing tasks.

Thus, a SWIFT algorithm for spectral analysis has been described and shown to be advantageous for applications that require successive calculations and real-time analysis. The SWIFT algorithms described in the present disclosure provide improved stability, reduces computational complexity and memory requirements, reduces spectral leakage, and improves frequency resolution. Additionally, the αSWIFT implementation has been described, which further reduces spectral leakage and reduces noise.

Figure 6:
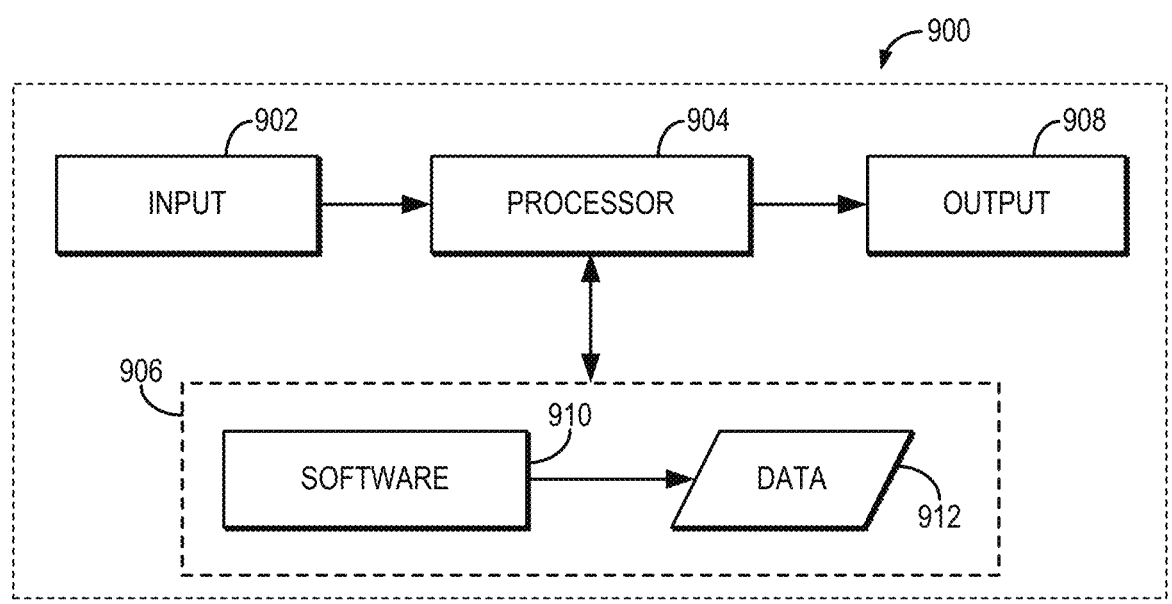
FIG. 6 is a block diagram of an example computer system that can implement the methods described in the present disclosure.

Referring now to FIG. 6, a block diagram of an example of a computer system 900 that can perform the methods described in the present disclosure is shown. The computer system 900 generally includes an input 902, at least one hardware processor 904, a memory 906, and an output 908. Thus, the computer system 900 is generally implemented with a hardware processor 904 and a memory 906.

In some embodiments, the computer system 900 can be a digital spectrum analyzer for computing the sliding windowed infinite Fourier transform coefficients from a number, N, of digitized samples of input signal data. The computer system 900 may also be implemented, in some examples, by a workstation, a notebook computer, a tablet device, a mobile device, a multimedia device, a network server, a mainframe, one or more controllers, one or more microcontrollers, or any other general-purpose or application-specific computing device. In some implementations, the computer system 900 can be part of an embedded device, such as an implantable medical device, which may include a CIED or an implantable neural stimulation device.

The computer system 900 may operate autonomously or semi-autonomously, or may read executable software instructions from the memory 906 or a computer-readable medium (e.g., a hard drive, a CD-ROM, flash memory), or may receive instructions via the input 902 from a user, or any another source logically connected to a computer or device, such as another networked computer or server. Thus, in some embodiments, the computer system 900 can also include any suitable device for reading computer-readable storage media.

In general, the computer system 900 is programmed or otherwise configured to implement the methods and algorithms described in the present disclosure. For instance, the computer system 900 can be programmed to compute a SWIFT or αSWIFT of input signal data.

The input 902 may take any suitable shape or form, as desired, for operation of the computer system 900, including the ability for selecting, entering, or otherwise specifying parameters consistent with performing tasks, processing data, or operating the computer system 900. In some aspects, the input 902 may be configured to receive data, such as data acquired with a physiological measurement device, an auditory signal measurement device, and so on. Such data may be processed as described above to extract signal feature data of the input signal data, such as amplitude, phase, or frequency information of the input signal data. In addition, the input 902 may also be configured to receive any other data or information considered useful for implementing the SWIFT and αSWIFT algorithms described above, such as parameters for constructing one or more infinite-length window functions.

Among the processing tasks for operating the computer system 900, the one or more hardware processors 904 may also be configured to carry out any number of post-processing steps on data received by way of the input 902.

The memory 906 may contain software 910 and data 912, such as input signal data, and may be configured for storage and retrieval of processed information, instructions, and data to be processed by the one or more hardware processors 904. In some aspects, the software 910 may contain instructions directed to implementing the SWIFT and αSWIFT algorithms described in the present disclosure.

In addition, the output 908 may take any shape or form, as desired, and may be configured for displaying input signal data, signal feature data, or other desired information.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

The present disclosure has described one or more preferred embodiments, and it should be appreciated that many equivalents, alternatives, variations, and modifications, aside from those expressly stated, are possible and within the scope of the invention.

The invention claimed is:

1. A method for controlling a neural stimulation device, the steps of the method comprising:
  (a) providing to a computer system, input signal data comprising a plurality of samples acquired with a measurement device, wherein the input signal data comprise physiological signal data acquired with a physiological measurement device, wherein the physiological measurement device is an EEG device and the physiological signal data indicates neural signals in a subject;

(b) generating signal feature data with the computer system by applying a sliding windowed infinite Fourier transform to the input signal data by:
  (i) selecting with the computer system, a window function comprising an infinite-length function having a time constant with units of number of samples;
  (ii) initializing a discrete-time Fourier transform (DTFT) matrix with the computer system;
  (iii) updating the DTFT matrix by:
    phase shifting the DTFT matrix by an angular frequency;
    decaying an amplitude of the DTFT matrix using the time constant;
    selecting a next sample in the input signal data and adding the next sample to the DTFT matrix;
  (iv) repeating step (iii) for a selected number of samples in the input signal data in order to generate the signal feature data;
(c) storing the signal feature data generated by the computer system, wherein the signal feature data comprises at least one of amplitude information of the input signal data, phase information of the input signal data, or frequency information of the input signal data;
(d) transforming the signal feature data into a set of control signals for controlling the neural stimulation device, wherein the set of control signals are indicative of one or more operating parameters for delivering an electrical stimulation by the neural stimulation device; and
(e) controlling the neural stimulation device using the set of control signals.

2. The method as recited in claim 1, wherein the infinite-length window function is an infinite-length exponential function.

3. The method as recited in claim 2, wherein the infinite-length exponential function is, $$w[m] = \begin{cases} e^{m/\tau} & m \leq 0 \\ 0 & m > 0 \end{cases};$$

wherein m are samples in the input signal data, m=0 is a current sample, and $\tau$ is the time constant of the window function.

4. The method as recited in claim 1, wherein the infinite-length window function comprises a difference between a first infinite-length exponential function having a first time constant and a second infinite-length exponential function having a second time constant that is different from the first time constant.

5. The method as recited in claim 4, wherein the infinite-length window function is, $$w_a[m] = \begin{cases} e^{m/\tau_{slow}} - e^{m/\tau_{fast}} & m \leq 0 \\ 0 & m > 0 \end{cases};$$

wherein m are samples in the input signal data, m=0 is a current sample, $\tau_{slow}$ is the first time constant, and $\tau_{fast}$ is the second time constant.

6. The method as recited in claim 1, wherein step (b)(iv) includes decaying the amplitude of the DTFT by $e^{-1/\tau}$, wherein $\tau$ is the time constant of the window function.

7. The method as recited in claim 1, wherein initializing the DTFT matrix comprises computing a DTFT matrix of the input signal data over the selected window.

8. The method as recited in claim 1, wherein initializing the DTFT matrix comprises setting values in the DTFT matrix to selected initial values.

9. The method as recited in claim 8, wherein the selected initial values comprise zeros.

10. A method for controlling a brain-computer interface, the steps of the method comprising:
(a) providing to a computer system, input signal data comprising a plurality of samples acquired with a measurement device, wherein the input signal data comprise physiological signal data acquired with a physiological measurement device, wherein the physiological measurement device is an EEG device and the physiological signal data indicates neural signals in a subject;
(b) generating signal feature data with the computer system by applying a sliding windowed infinite Fourier transform to the input signal data by:
  (i) selecting with the computer system, a window function comprising an infinite-length function having a time constant with units of number of samples;
  (ii) initializing a discrete-time Fourier transform (DTFT) matrix with the computer system;
  (iii) updating the DTFT matrix by:
    phase shifting the DTFT matrix by an angular frequency;
    decaying an amplitude of the DTFT matrix using the time constant;
    selecting a next sample in the input signal data and adding the next sample to the DTFT matrix;
  (iv) repeating step (iii) for a selected number of samples in the input signal data in order to generate the signal feature data;
(c) storing the signal feature data generated by the computer system, wherein the signal feature data comprises at least one of amplitude information of the input signal data, phase information of the input signal data, or frequency information of the input signal data;
(d) transforming the signal feature data into a set of control signals for controlling the brain-computer interface, wherein the set of control signals are associated with one or more operating parameters for controlling the brain-computer interface; and
(e) controlling the brain-computer interface using the set of control signals, wherein controlling the brain-computer interface using the set of control signals includes further controlling, via the brain-computer interface, operation of a device in communication with the brain—computer interface.

11. The method as recited in claim 10, wherein the device in communication with the brain-computer interface is a prosthetic device, such that the brain-computer interface controls operation of the prosthetic device using the set of control signals transformed from the signal feature data.

12. A method for controlling a cochlear implant, the steps of the method comprising:
(a) providing to a computer system, input signal data comprising a plurality of samples acquired with a measurement device, wherein the input signal data comprise auditory signal data;
(b) generating signal feature data with the computer system by applying a sliding windowed infinite Fourier transform to the input signal data by:

(i) selecting with the computer system, a window function comprising an infinite-length function having a time constant with units of number of samples;
(ii) initializing a discrete-time Fourier transform (DTFT) matrix with the computer system;
(iii) updating the DTFT matrix by:
    phase shifting the DTFT matrix by an angular frequency;
    decaying an amplitude of the DTFT matrix using the time constant;
    selecting a next sample in the input signal data and adding the next sample to the DTFT matrix;
(iv) repeating step (iii) for a selected number of samples in the input signal data in order to generate the signal feature data;
(c) storing the signal feature data generated by the computer system, wherein the signal feature data comprises at least one of amplitude information of the input signal data, phase information of the input signal data, or frequency information of the input signal data;
(d) transforming the signal feature data into a set of control signals for controlling the cochlear implant, wherein the set of control signals are indicative of one or more operating parameters for generating one or more electrical simulation pulses with the cochlear implant; and
(e) controlling the cochlear implant to generate the one or more electrical simulation pulses using the set of control signals.

13. The method as recited in claim 12, wherein controlling the cochlear implant includes using phase information in the signal feature data to provide phase-locked stimulation of a cochlear nerve.

* * * * *

UNITED STATES PATENT AND TRADEMARK OFFICE
CERTIFICATE OF CORRECTION

PATENT NO. : 11,468,144 B2
APPLICATION NO. : 16/009829
DATED : October 11, 2022
INVENTOR(S) : Logan L. Grado et al.

It is certified that error appears in the above-identified patent and that said Letters Patent is hereby corrected as shown below:

In the Specification

Column 6, Line 61, Eq. (1), "$X_n[k]=X_{n-1}[k]e^{j2\pi k/N-x[n-N]+x[n]}$" should be
--$X_n[k]=X_{n-1}[k]e^{j2\pi k/N}-x[n-N]+x[n]$--.

Signed and Sealed this
Twentieth Day of December, 2022

Katherine Kelly Vidal
*Director of the United States Patent and Trademark Office*